Figure 1:
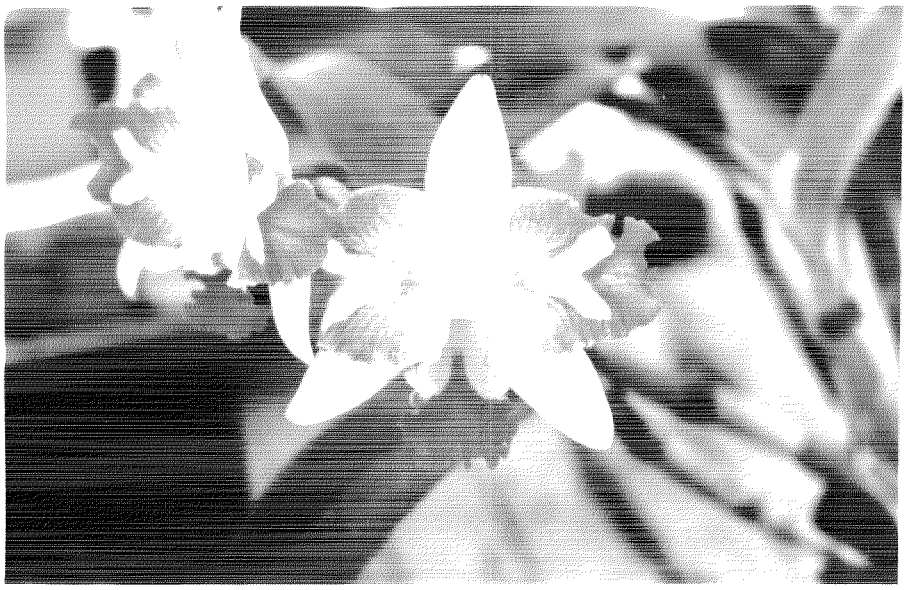

US00PP10243P

United States Patent [19]

Elmore

[11] Patent Number: Plant 10,243

[45] Date of Patent: Feb. 17, 1998

[54] SOPHROLAELIOCATTLEYA BARBARA ELMORE PLANT 'HEARTS'

[76] Inventor: James Lewis Elmore, 324 Watt Rd., Knoxville, Tenn. 37922

[21] Appl. No.: 675,097

[22] Filed: Jul. 3, 1996

[51] Int. Cl.[6] ..... A01H 5/00

[52] U.S. Cl. ..... Plt./87.3

[58] Field of Search ..... Plt./87.3

*Primary Examiner*—James R. Feyrer
*Assistant Examiner*—Kent L. Bell

[57] ABSTRACT

A new and distinct variety of orchid and more particularly a Sophrolaeliocattleya (Slc.) hybrid plant which is outstanding and distinct from other orchids because of its unique color pattern of a yellow heart-shaped splash in the petals surrounded by purple coloration, its flower form which is consistently flat and fully open, and its flower carriage high above the foliage on a tall stem. The heart-shaped pattern is consistently well formed and different from other orchids. The flowers are considerably larger and of consistently better shape than any of its siblings in the grex population or similar hybrids. The substance of the flowers is superior to its siblings, resulting in longer lasting flowers. The new variety exhibits more vigorous growth than its siblings and other similar hybrids.

1 Drawing Sheet

DISCOVERY OF THE NEW VARIETY

The orchid of the application was discovered by the undersigned in 1988 at its first blooming as an outstanding member of a large sibling population of the hybrid Sophrolaeliocattleya Barbara Elmore (hereinafter abbreviated Slc. Barbara Elmore). All were cultivated and bloomed at the Elmore Orchids nursery in Knoxville, Tenn.

This plant is a hybrid orchid plant (Family: Orchidaceae) from a cross between Sophrolaeliocattleya (Slc.) Kauai Starbright and Cattleya (C.) Okami. Slc. Kauai Starbright was the pod parent. This grex was registered by the Elmore Orchids nursery with the Orchid Registration Committee of The Royal Horticultural Society in England in 1990 as Slc. Barbara Elmore.

As other plants of Slc. Barbara Elmore were flowered, it eventually became apparent that this plant was superior in its flowers to all other siblings of the population. Observations of the new variety over several years lead to the discovery of its flowering consistency, superior vigor, and compact growth form. The cultivar name "Hearts" was given to the plant after it was awarded an Award of Merit from the American Orchid Society (AM/AOS) in 1993, granted to Elmore Orchids. This cultivar name allows this plant to be distinguished from all other siblings of the grex.

ASEXUAL REPRODUCTION

After the "Hearts" cultivar was discovered, the plant was asexually reproduced by meristem tissue culture. A new growth was sent by Elmore Orchids to Island Cultures in Hawaii where the tissue culture was performed. All of the flasks containing all the tissue cultured plants were returned to Elmore Orchids. The tissue cultured plants were potted into community pots (ten to twenty plants per pot). Subsequently, the community pots have been repotted with individuals now residing in 2 inch, 3 inch, and 4 inch pots. All of these plants were asexual reproductions from the original cultivar. None of these plants, either original or tissue cultured plants, have been released. All plants of this cultivar still reside in greenhouses at the Elmore Orchids nursery.

DESCRIPTION OF PHOTOGRAPHS

FIG. 1—Close up of the flowers.

Figure 2:
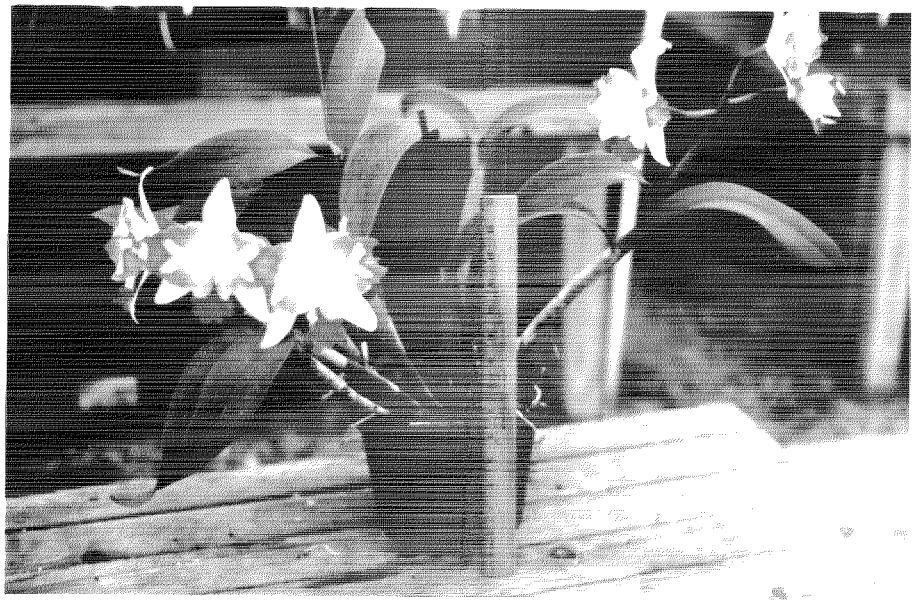

FIG. 2—Entire plant including flowers.

DESCRIPTION OF THE PLANT

The plant of the new variety has a typical cattleya growth habit with strap like, usually bifoliate, coriaceous leaves. The mature plant stands approximately 14 to 18 inches (36 to 46 cm) tall, excluding inflorescence. The inflorescence is approximately 8 to 10 inches (20 to 25 cm) long and the main stem of the inflorescence is about 5 to 7 inches (13 to 18 cm) long. Pseudobulbs are approximately 9 to 12 inches (23 to 30 cm) long with bifoliate leaves about 1.7 to 2.2 inches (4 to 6 cm) wide by 8 to 10 inches (20 to 25 cm) long. Plant color is typically plain green without markings. Flower stems, leaves, and other plant parts are thicker and heavier than other cultivars of the grex Slc. Barbara Elmore. "Hearts" grows with greater vigor and strength than the other cultivars of the grex. The rhizome is compact growing, branching freely into flowering leads. The flower stem supports the flowers well, with the flowers well separated and displayed. The flower sheath is borne in the axil of the growth with the flowers carried well above the foliage.

The plants are vigorous and uniform in comparison with similar siblings or cultivars of other gregi. All plants of this cultivar have been virus and pathogen free during their development. There have been no manifestations of aberrant growth habit. The "Hearts" cultivar has been used in hybridizing and found to be an outstanding parent, especially exceptional in the area of seed production. This new cultivar may well be a tetraploid.

DESCRIPTION OF THE FLOWER

The most outstanding and distinguishing features of the new variety are the unique color pattern of the flowers, their outstanding flat open form, and their carriage well above the foliage.

In the following description, the principle colors will be specified by reference to code numbers in the R.H.S. Colour Charts (The Royal Horticultural Society, 1995). The flowers have sepals and petals that are light cream-color (R.H.S. Colour Chart 155B); the petals are overlaid with light purple (R.H.S. Colour Chart 78B) striated basally, with a yellow (R.H.S. Colour Chart 7A) heart-shaped splash centrally located; the lip is yellow (R.H.S. Colour Chart 9A)at the base, with a dark purple (R.H.S. Colour Chart 78A) apex, and the column is a light cream-color. The substance is firm and the texture is satin. The flowers hold their color especially well compared to other siblings and gregi of this line of breeding.

Sepals are essentially pure white to cream; and bluntly attenuate with entire margins. Petals are about twice the width of sepals, and somewhat longer. Petal margins are ruffled at the apex. The column has the coloration of the sepals, is of abreviated size, and has the shape of a human proboscus. The column is partially hooded by outward flaring basal extensions of the labellum. The margin of the labellum subtending the flaring extensions is ruffled as best shown in the top photograph. The coloration and pattern of labellum markings are similar to those of the petals.

The flowers are substantially larger and with heavier substance than other cultivars of Slc. Barbara Elmore. Natural lateral spread of the flower is approximately 3.5 to 4 inches (9 to 10 cm) with a vertical height of 3.7 to 3.9 inches (9 to 10 cm). The dorsal sepal is 0.9 to 1.1 inches (2.4 to 2.8 cm) wide and 2.5 to 2.7 inches (6.3 to 6.9 cm) long. Petals are 1.6 to 1.7 inches (4.2 to 4.3 cm) wide and 2.0 to 2.2 inches (5.2 to 5.6 cm) long. Lateral sepals are 1.0 to 1.1 inches (2.5 to 2.8 cm) wide and 2.4 to 2.6 inches (6.0 to 6.6 cm) long. The labellum is 1.2 to 1.3 inches (3.2 to 3.3 cm) wide by 2.0 to 2.2 inches (5.2 to 5.6 cm) long.

Number of blooms per inflorescence ranges typically from three to six on mature plants. The flowers are well-positioned on the stem and are always well formed and fully open, unlike many of the other gregi of this line of breeding (splash-petal cattleyas). This plant normally blooms in November and December.

The flowers retain their shape and color for up to six weeks, a longer time than most orchids of similar Breeding. The flowers of the new variety have a pleasant fragrance throughout their life.

The above combination of superior characteristics of this new cultivar make it especially valuable to the commercial pot plant grower looking for a product for the Christmas holiday season and to the connoisseur who may seek a different look in a vigorous growing orchid plant. It is also especially useful to the orchid breeder wanting to breed for a unique combination of traits.

I claim:

1. A new and distinct variety of a hybrid Sophrolaeliocattleya orchid plant, substantially as described and illustrated herein which is distinguished from siblings of this grex, Slc. Barbara Elmore, and other orchids by its combination of a unique color pattern of a yellow heart-shaped splash in the petals surrounded by purple coloration, flower shape which is consistently flat and fully open, superior flower substance, flower carriage high above the foliage on a tall stem, its vigorous growth, and reliable uniform blooming.

* * * * *